(12) United States Patent
Badorrek et al.

(10) Patent No.: US 9,103,804 B2
(45) Date of Patent: Aug. 11, 2015

(54) TRACE ANALYTE EXTRACTION USING ADSORPTIVE CARBIDE-DERIVED NANOPOROUS CARBON POWDERS

(71) Applicant: BAE Systems Information and Electronic Systems Integration Inc., Nashua, NH (US)

(72) Inventors: Christopher S. Badorrek, Hagerstown, MD (US); Robert A. Burton, Columbia, MD (US); Tadd C. Kippeny, Mount Airy, MD (US); Louise C. Sengupta, Ellicott City, MD (US); Laura A. Swafford, Baltimore, MD (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 293 days.

(21) Appl. No.: 13/826,939

(22) Filed: Mar. 14, 2013

(65) Prior Publication Data

US 2014/0020447 A1 Jan. 23, 2014

Related U.S. Application Data

(60) Provisional application No. 61/672,543, filed on Jul. 17, 2012.

(51) Int. Cl.
*G01N 30/00* (2006.01)
*G01N 1/40* (2006.01)
*B01J 20/02* (2006.01)
*B01J 20/20* (2006.01)
*B01J 20/28* (2006.01)
*G01N 30/72* (2006.01)

(52) U.S. Cl.
CPC .................. *G01N 30/00* (2013.01); *B01J 20/02* (2013.01); *B01J 20/20* (2013.01); *B01J 20/28004* (2013.01); *B01J 20/28066* (2013.01); *B01J 20/28078* (2013.01); *G01N 1/405* (2013.01); *G01N 30/7233* (2013.01); *G01N 2030/009* (2013.01)

(58) Field of Classification Search
CPC ......... G01N 1/02; G01N 1/405; G01N 30/00; G01N 30/7233; G01N 2001/007; G01N 2030/009
See application file for complete search history.

(56) References Cited

U.S. PATENT DOCUMENTS

2010/0107731 A1* 5/2010 Kippeny ...................... 73/23.41

OTHER PUBLICATIONS

Yamashita et al, Latent Print development, Chapter 7, p. 7-1-p. 7/67.*

* cited by examiner

*Primary Examiner* — Laura Martin
*Assistant Examiner* — Alex Devito
(74) *Attorney, Agent, or Firm* — Daniel J. Long

(57) ABSTRACT

In the method of latent print analysis, wherein the improvement comprises using an ultra-fine, nanoporous carbon material as an adsorptive powder to identify trace chemicals found within oils of a print.

11 Claims, 2 Drawing Sheets

TRACE ANALYTE EXTRACTION USING ADSORPTIVE CARBIDE-DERIVED NANOPOROUS CARBON POWDERS

RELATED APPLICATIONS

This application claims the benefit of U.S. Provisional Application No. 61/672,543, filed Jul. 17, 2012 which is herein incorporated by reference in its entirety for all purposes.

FIELD OF THE INVENTION

The present invention relates to methods of extraction and chemical separation, liquid chromatography or batch analyte extraction procedures that employ carbide-derived nanoporous carbons, and more particularly to methods of detecting trace chemicals in latent fingerprints using adsorptive powders.

BACKGROUND OF THE INVENTION

Liquid and liquefied gas (i.e. supercritical $CO_2$ phase chromatography and extraction is usually founded upon principles of size or charge differentiation among molecules to be separated. Size exclusion chromatography (separation based on size) and ion exchange or hydrophobic chromatography (separation based on charge) can also be combined for complex chemical separation parameters. However, chemical separation is often inadequate resulting in broad or overlapping chemical elution profiles.

Many types of solid phase material are used for liquid chromatography separations and extractions including micron-sized particles of silica gel, alumina, and high and low density polymer beads. Current methodologies can lead to broad chromatographic analyte peaks that can overlap, limiting the purity of the end product and increasing the labor and time required for liquid chromatography purification schemes. Sorption of liquids or gases onto the current material and extraction is difficult.

Despite this difficulty, analyte analysis remains an important part of many procedures including forensic research. For example, during crime scene investigations, surfaces are frequently swabbed in an attempt to salvage material for analyte analysis through various methods including liquid chromatography.

Many of the analytes salvaged during such swabbing includes secretions from skin of individuals who were present in the location being analyzed. These secretions contain perspiration, body oils and trace quantities of loose material that an individual comes in contact with such as organic compounds, amino acids, lipids, drugs, sulfonamides, antipyrine, acetaminophen, aminopyrine, L-dimethylamphetamine, L-methamphetamine, carbohydrates, cholesterol, iron, C19-steroid sulfates, and Δ16-steroids. These trace chemicals, or analytes, are transferred from the skin along with grease, oil, and perspiration to other surfaces when contact is made with other objects. Analysis and identification of these analytes from fingerprint residue is then used to provide insight into the suspect's habits and evidence of illicit activity.

A fingerprint in its narrow sense is an impression left by the friction ridges of a human finger. In a wider use of the term, fingerprints are the traces of an impression from the friction ridge formations, or patterns of the raised portions, found on the fingertips. These friction ridge formations are unique to an individual, so that no two persons have the exact same fingerprint.

Fingerprint identification is the common term for the process of comparing two instances of friction ridge skin impressions for the purposes of determining whether these impressions could have come from the same individual. Current latent print analysis allows investigators to identify persons of interest by comparing the ridge detail patterns of prints with databases of known prints.

Collecting latent prints involves the application of ultrafine carbon black powder to the latent print deposited body oils and waxes that are transferred to a surface or substrate upon contact. Interaction between the printing powder and the deposited oils results in the visualization of the ridges and whorls within a print. The lifted print image can then be uploaded to biometric analysis databases such as the FBI IAFIS for future reference.

For these reasons, fingerprint impressions, through analyte analysis and visual impression analysis and comparison, offer a means of personal identification.

However, frequently, the detected print does not match any print on file. When this occurs, the print does not assist in investigation until such time as the print can be linked to an individual through outside means (i.e., if the suspect gives a print as part of the current or other investigation). Additionally, inconclusive partial prints are frequent and limit the value of the obtained data through fingerprint identification. The presence and identification of latent prints simply establishes whether a given subset of individuals have ever been at a particular location. Intelligence on age, gender, physiology, habits, or activities can be inconclusive or impossible to obtain from a simple latent print image.

Another problem for current forensic teams is that the two methods of identifying suspects through fingerprint residue and visual impressions are mutually exclusive. Currently the two processes are mutually incompatible because the fingerprint developers destroy material that could potentially be used for DNA analysis and swabbing for analytes disturbs the visual impressions which make fingerprint identification impossible.

A need therefore exists for an improved separation and/or extraction method that can be achieved by using particles with pore size and pore size distribution and surface functionality that can be tailored to match the specific needs of a project. A need exists for an improved "soft" extraction method that will not destroy the substrate of the analytes.

SUMMARY OF THE INVENTION

The present invention is a novel method to provide adsorption, desorption, and analysis of analytes from is carbonaceous sorbent powder with improved quantitative results, and with reduced rearrangement of the adsorbed analytes.

In some embodiments, carbide-derived nanoporous carbons are fabricated with a wide range of defined particle sizes, and even as porous monoliths, that incorporate nano- and meso-scale pores that can be tuned in both size and distribution dependent upon starting carbide material and fabrication parameters. Post-fabrication surface treatments are designed to alter the surface charge and polarity as desired. Together, these embodiments provide a widely tunable, extremely high surface area material for utilization with liquid phase separations and extractions. Liquid chromatography columns or batch analyte extraction procedures that employ nanoporous CDC carbons greatly outperform current methodologies.

In one general embodiment of the present invention the sorbent is used as a powder for collecting latent prints and identifying trace analytes contained within the oils of the print. This process involves four distinct steps: adsorption of print oils and trace analytes by the powder, capturing a visual image of the print, desorption of print oils and trace analytes into a chemical analysis system, and identification of trace analytes by the chemical analysis system.

These analytes can be: (a) biological indicators that relay information about the suspect's gender, age, race, medical status (for example, diabetic), etc.; (b) chemical indicators that relay information on habits or where the suspect has been (for example, suspect is a smoker or has been near a specific manufacturing plant); and (c) chemical indicators that relay information on illegal activities (for example, suspect has handled explosives or illegal drugs). By identifying these trace chemicals, one embodiment of the present invention allows insight into a suspect's identity and activities even when the print cannot be identified by ridge detail. This will lead to more insight into the individual's chemical history and provide additional information for sensitive site exploitation, including evidence of illicit activity.

Those skilled in the art will appreciate that the present invention involving liquid chromatography and extraction using tailored nanoporous carbons is expected to increase the total efficiency of liquid chromatography by decreasing elution peak width and increasing peak separation adding major advantages to standard latent print analysis. No longer will forensic scientists have to choose between fingerprint identification or secretion analysis. If the suspect's prints are not available for comparison to the unidentified print, the analytes contained within the latent print can still be used to narrow down the identity of the suspect based on biological markers.

BRIEF DESCRIPTION OF THE DRAWINGS

The present invention is further described with reference to the following drawings wherein.

DETAILED DESCRIPTION

Figure 1:
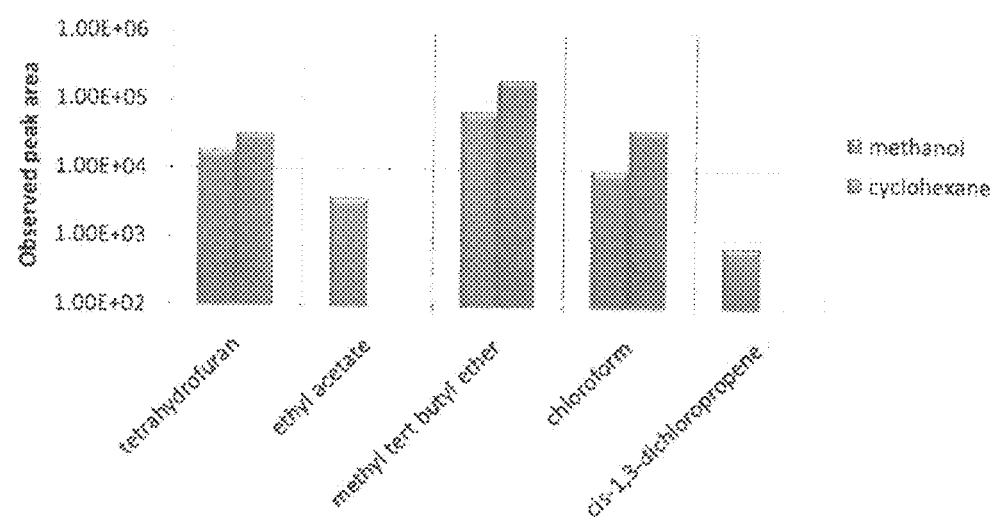
FIG. 1 is a graphical representation of selective analyte extraction using liquid chromatography/mass spectrometry from carbide derived carbons.

FIG. 1 is a graphical representation of some general embodiments of the invention utilizing simple polar and non-polar solvents. These embodiments utilized ultra-fine nanoporous carbide derived carbon hydrophobic powder that adheres to deposited body oils and waxes and readily adsorbs chemicals to capture a wide variety of chemical analytes ranging from 10 to 100 ppb. However, as the graph indicates, instead of thermal desorption of the exposed nanoporous carbon material, the carbide derived carbon was subjected to either a polar (methanol) or non-polar (cyclochexane) solvent for five minutes. The solvent was then filtered injected (10 µL) into a CIS 4 coupled to an Agilent 6890 GC/5975 MS.

FIG. 1 shows a graph representing the selective extraction of analytes from nanoporous carbon via liquid solvent extraction. These results also show that selective analytes can be removed from nanoporous carbon by varying the type of solvent used during extraction.

Another general aspect of the present invention that may allow selective adsorption and desorption of analytes is through the alteration surface functional groups and shape of the basic carbon skeleton. This general nanoporous carbon skeleton is synthesized from a metal carbide (typically molybdenum, silicon, or titanium) that is processed with a gaseous halogen to chemically extract the metal leaving behind a highly porous (~2000 m2/g), hydrophobic carbon network.

By selectively choosing both the starting carbide and the metal extraction process parameters, a wide range of pore sizes can be obtained. The surface of the carbon skeleton can also be chemically modified through various processes to add specific functional groups to the surface. These modifications significantly alter the physiochemical interaction of the carbon skeleton with analytes through molecular size/shape and chemical interactions.

These various forms of carbide derived carbons skeletons and the effect upon the chemical interactions are well known in the art. For example, it has been experimentally shown that addition of fluorobenzene to the surface can change the capture/release response of nanoporous carbon to small polar analytes (e.g. ethyl alcohol) by 20 fold improvement. Similarly, various configurations of carbide-derived carbon materials, including 5 µm SiC and 350 µm Mo2C powders with 1-5 nm pores and various surface functionalizations, have been used to extract and separate components of liquid solutions. Carbide-derived carbon nanoporous sorbent materials can adsorb and bind both gas and liquid phase small molecule analytes as well as large biomolecules such as hemoglobin.

In some embodiments, these various sorbent materials are combined with liquid chromatography columns or batch analyte extraction procedures to greatly outperform current methodologies.

Again, as previously shown in FIG. 1, these embodiments may include differentially elution by using either polar or non-polar solvents and/or through a supercritical carbon dioxide extraction process. Data also shows that the levels of detection are dramatically improved when using the carbide-derived nanoporous carbon materials versus other currently available sorbent materials.

Figure 2:
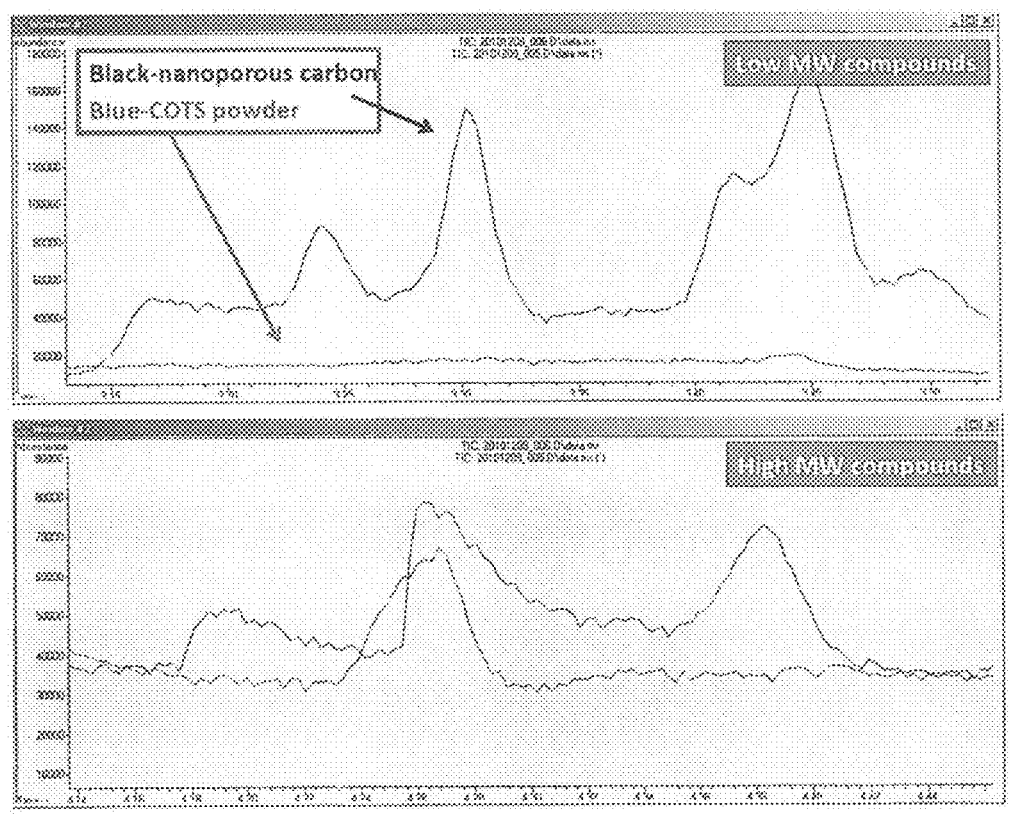
FIG. 2 is a graph displaying representative portions of gas chromatography/mass spectrometry extraction profiles from the carbide derived carbon (black) and conventional COTS powder (blue) lifted from latent prints.

FIG. 2 shows a graphical representation of one embodiment of the invention in which the solvent utilized for the extraction method is supercritical carbon dioxide. Extraction utilizing supercritical carbon dioxide provides many significant advantages over traditional solvents used in conventional forensic high performance liquid chromatography (HPLC). By taking advantage of the critical point of liquid carbon dioxide, dissolved analytes can be directly 'flashed' into the vapor phase without any thermal decomposition or rearrangements, leaving all of the materials within a peak of interest to be injected directly into a quadrupole mass spectrometer, and thereby greatly improving the analyte signal, especially for larger biological molecules (i.e. lipids and proteins).

Extraction utilizing supercritical carbon dioxide provides four significant advantages over traditional solvents used in HPLC. First, the polarity relationship of the supercritical carbon dioxide mobile phase can be continuously adjusted by changing the operating pressure providing an adjustable gradient elution from a single solvent. Second, it is a 'green' solvent with no disposal requirements. Third, in terms of larger biological molecules (i.e. lipids and proteins), this type of analysis is 'softer' than traditional solvents improving the integrity of the molecule during extraction. Finally, due to the critical point of liquid carbon dioxide, it can be used as a flash solvent allowing direct application of all dissolved analytes in the vapor phase into the mass spectrometer thereby limiting effects of thermal decomposition or rearrangements and greatly improving the analyte signal.

FIG. 2 also graphically represents an embodiment where the carbide derived carbon was utilized as a print powder and compared to the conventional COTS powder from lifted prints. Collected data suggests that the present embodiment outperforms the utilization of traditional COTS powder and analysis techniques in terms of both the types of chemicals detected and the quantity of each type of chemical.

One facet of this invention is the increased trace chemical adsorption. While any print powder will adsorb some degree of oils and chemicals, adsorption is maximized in various embodiments of this invention through the use of high surface area powders. This includes, but is not limited to, nanoporous powders and powders with nanoscale particle size. Adsorption can also be enhanced through use of powders whose surfaces readily interact with and trap the chemical in a reversible manner.

In some embodiments, carbide derived carbons were shown to adsorb and desorb virtually every chemical tested, including compounds associated with explosives and drug manufacturing precursors. The chemicals, which ranged in both size and chemical class/functionality, were detected at concentrations ranging from 1% down to 100 parts per trillion (gas phase) and were identified using conventional gas chromatography/mass spectrometry (GC/MS).

Also, the nanoporous carbon has been demonstrated to operate at 85% relative humidity environment with minimal change in performance due to water adsorption. Thus, nanoporous carbons appear optimal for specific environmental fingerprint analytes of interest such as explosives, narcotics, and biomarkers.

Another general aspect of this invention allows a visual representation of a fingerprint to be gathered before the analytes are extracted from the powder and analyzed for content. This is possible without further chemical manipulation because the carbide derived carbon sorbent is a strong black body light absorber. The carbide derived carbon powder adheres preferentially to the oils in the print, yielding a visible image of the print. As previously discussed, the powder that is lifted carries with it some of the oils and trace analytes to which it had originally adsorbed and can now be analyzed. However, the print that is lifted from the substrate material can now also be imaged in place with a camera. For these embodiments then, the fingerprint analysis and fingerprint identification can be done using the same carbon powder.

An experiment was performed to compare carbide derived carbon powder utilized as a fingerprint powder against two different current latent powders, Lynn Peavy powder and Lightning powder. The experiment was performed on a first non-porous surface: ceramic. The experiment was also performed on another distinct non-porous surface: paint can lids.

For both experiments, test surfaces were cleaned thoroughly using methanol (MeOH) in a well-ventilated hood. The surfaces were then dried using standard Kimwipes to ensure that there is no residual organic solvent. A 6"×6" off-white, smooth ceramic surface was divided into quadrants to perform a comparative study between various latent print powders. Four individual paint lids were used to study latent prints on metal surfaces. In both cases a blank print with no powder was made as a control. The protocol requires a participant to rub their thumb onto their forehead to effectively build up sebaceous oils after which he or she will place their print onto the test surface. The sample was left out for a period of 1 hour before being dusted by the powder of interest. Excess powder was removed from the surface and a dusted print was visualized using optical photography. The print was then removed from the surface using a print lifting tape and placed on a labeled print card. To ensure repeatability, all samples were produced in duplicate.

The results from the side by side comparative analysis of the print powders used on ceramic tiles containing latent prints are shown in FIG. 3. The present embodiment appears to bind to the oils in the latent print just as effectively (if not better) than the conventional COTS powders: Lynn Peavey or Lightning powder. Also, the present embodiment appeared to conserve the print as good if not better than the other COTS powders after being lifted with print tape and placed on a print card.

From the results from the side by side comparative analysis of the print powders used on paint can lids containing latent prints the present embodiment again appears to bind to the oils in the latent print just as effectively (if not better) than the conventional COTS powders: Lynn Peavey or Lightning powder.

The present embodiment appeared to conserve the print as well if not better than the other COTS powders after being lifted with print tape and placed on a print card. Print resolution obtained with this embodiment nanoporous carbon powder was superior to that of the COTS powder and approximated that of a direct ink pad print.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto It is claimed:

1. A method of chemical analyte analysis comprising the steps of utilizing a carbon material comprising a carbide-derived carbon skeleton and a functional group and having a plurality of nanopores having a mean nanopore diameter within the range of about 1 nm to about 5 nm; collecting latent fingerprints; allowing the carbon material to absorb analytes from the latent fingerprints; extracting analytes with a supercritical carbon dioxide solvent from a latent fingerprint; and analyzing analytes with liquid chromatography, wherein said carbon material further comprises a particle size within the range of about 5 um to about 10 um which has a surface area to weight ratio of about 1,000 m2/g to about 2500 m2/g.

2. The method of claim 1 wherein said hyperadsorbent carbon material further comprises: a particle size of about 5 um; and a surface area to weight ratio of about 2500 m2/g and having a mean nanopore diameter of about 5 nm.

3. The method of claim 2 wherein extracting analytes with a supercritical carbon dioxide solvent from a latent fingerprint further comprises utilizing a front end supercritical carbon dioxide extraction system.

4. The method of claim 2 wherein extracting analytes with a supercritical carbon dioxide solvent from a latent fingerprint further comprises extracting the analytes without disturbing said latent fingerprint.

5. The method of claim 1 wherein the functional group is selected from the group consisting of metal carbide, molybdenum, silicon, and/or titanium.

6. The method of claim 1 wherein extracting analytes from a latent fingerprint further comprises the step of using a non-polar solvent.

7. The method of claim 1 wherein extracting analytes from a latent fingerprint further comprises the step of using a polar solvent.

8. The method of claim 1 wherein analyzing analytes further comprises the step of utilizing a gas chromatograph mass spectrometer.

9. The method of claim 1 wherein analyzing analytes further comprises the step of utilizing a quadropole mass spectrometer.

10. The method of claim 1 wherein analyzing analytes further comprises the step of utilizing a high performance liquid chromatograph.

11. The method of claim 1 wherein analyzing analytes further comprises the step of utilizing said high performance liquid chromatography which is performed with supercritical carbon dioxide.

* * * * *